(12) United States Patent
Kelsch et al.

(10) Patent No.: US 6,592,730 B1
(45) Date of Patent: Jul. 15, 2003

(54) DURABLE CARBON ELECTRODE

(75) Inventors: Daniel N. Kelsch, Fairview Park, OH (US); Iain F. McVey, Lakewood, OH (US); Jan J. Lewandowski, South Euclid, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/499,479

(22) Filed: Feb. 7, 2000

(51) Int. Cl.$^7$ ................................................ G01N 27/26
(52) U.S. Cl. .................... 204/412; 134/56 R; 134/58 R; 204/286.1; 204/294; 204/297.01; 204/400; 205/787
(58) Field of Search .............................. 204/400, 412, 204/294, 286.1, 297.01

(56) References Cited

U.S. PATENT DOCUMENTS

| | | | |
|---|---|---|---|
| 2,816,069 A | * | 12/1957 | Andrus |
| 3,560,365 A | * | 2/1971 | Mueller |
| 3,644,824 A | | 2/1972 | Barker et al. |
| 4,216,069 A | | 8/1980 | Olson |
| 4,571,292 A | | 2/1986 | Liu et al. |
| D292,229 S | | 10/1987 | Knudson et al. |
| 4,882,029 A | * | 11/1989 | Eickmann |
| 4,897,162 A | | 1/1990 | Lewandowski et al. |
| 4,947,153 A | | 8/1990 | Berger |
| 4,959,130 A | * | 9/1990 | Josowicz et al. |
| 5,131,999 A | | 7/1992 | Gunasingham |
| 5,214,964 A | | 6/1993 | Hartfiel |
| 5,310,524 A | | 5/1994 | Campbell et al. |
| 5,364,510 A | | 11/1994 | Carpio |
| 5,366,609 A | | 11/1994 | White et al. |
| 5,374,892 A | | 12/1994 | Sturrock et al. |
| 5,380,422 A | * | 1/1995 | Negishi et al. |
| 5,395,493 A | | 3/1995 | Pinkowski |
| 5,400,818 A | | 3/1995 | Cosentino et al. |
| 5,470,484 A | | 11/1995 | McNeel |
| 5,494,637 A | | 2/1996 | Barlow |
| 5,503,720 A | | 4/1996 | Teske |
| 5,644,501 A | | 7/1997 | Lin et al. |

FOREIGN PATENT DOCUMENTS

| | | |
|---|---|---|
| DE | 4412576 | * 10/1995 |
| EP | 0333246 A2 | 3/1989 |
| JP | 01153470 | 6/1989 |
| WO | WO 9222808 | 12/1992 |
| WO | WO 9623215 | 8/1996 |

OTHER PUBLICATIONS

Analytical Chemistry, vol. 62, No. 10, May 15, 1990 (pp. 589A–597A).

* cited by examiner

*Primary Examiner*—T. Tung
(74) *Attorney, Agent, or Firm*—Fay, Sharpe, Fagan, Minnich & McKee, LLP

(57) ABSTRACT

An electrochemical analysis system includes a chamber (34) that defines a fluid receiving reservoir therein. A working electrode (40), a reference electrode (42), and a counter electrode (44) is mounted to the chamber. An electrochemical analysis circuit (38) applies appropriate voltages to the electrodes and reads appropriate currents from the electrodes to provide an indication of the peroxyacetic acid concentration in a sample. The working electrode includes a glassy carbon rod (60) which is surrounded by a compressible polymeric sleeve (64) and a metal sleeve (66). One end of the metal sleeve is swaged (68) to form a fluid tight compression seal with the insulating sleeve and the glassy carbon rod. An electrically conductive thermal extension joint between the glassy carbon rod and an electrically conductive rod (70) includes a bore (72) in the conductive rod in which the glassy carbon rod is slidably received and a compressed spring (74) in the bore.

30 Claims, 2 Drawing Sheets

DURABLE CARBON ELECTRODE

BACKGROUND OF THE INVENTION

The present invention relates to the electrode art. It finds particular application in conjunction with carbon electrodes for use in peracetic acid detectors and will be described with particular reference thereto. It is to be appreciated, however, that the invention will also find application in conjunction with carbon-based electrodes for use in other electrochemical applications.

Heretofore, in liquid-based sterilization systems, a premeasured dose of a strong oxidant antimicrobial agent, such as peracetic acid or reagents which react to form peracetic acid, hydrogen peroxide, chlorides, hydrochlorite, and other strong oxidants, was added to each disinfection or sterilization cycle. Strong oxidants react with the microbes and other contaminants that may be in the system. In medical applications, a blood residue is a strong oxygen scavenger. To determine whether an appropriate concentration of the antimicrobial agent was maintained in solutions for an appropriate time, biological and chemical indicators were typically placed with the items to be disinfected or sterilized in the processor. After the cycle, these indicators were incubated and examined, colorimetrically examined, or otherwise examined to provide a pass/fail indication of the success of the disinfection or sterilization cycle. While it would be advantageous to provide a real time parametric monitoring of the antimicrobial agent concentration, cost effective, accurate, reliable, and long-lived monitors have proved elusive.

One particular promising electrochemical sensor includes three electrodes, a working electrode, a counter electrode, and a reference electrode which are emersed in this liquid to be monitored. Metallic counter electrodes and silver/silver chloride reference electrodes which can be immersed in the strong oxidants for extended periods are available at a relatively reasonable cost. However, the ideal glassy carbon working electrode tends to be fragile, expensive, and has a relatively short working life.

Prior art carbon electrodes typically include a short rod of a glassy carbon, a brittle fragile material. A glassy carbon rod is commonly interfaced electrically with a metallic electrode rod using a graphite or other conductive grease. The peripheral surface of the carbon rod, the electrode rod, and the grease interface is surrounded by a plastic sheath, e.g., a heat shrunk plastic sheath. The face of the glassy carbon electrode is polished, typically hand polished. Unfortunately, the plastic sleeve does not adhere tightly to the carbon electrode under all normal operating conditions. For example, when mounted in a sealed fitting, the plastic sleeve tends to separate from the carbon allowing the monitored solution to pass in between. This provides both an escape path for the conductive graphite grease and an entrance path for the analyzed solution to degrade the grease and the metal electrode. Further, fluid access along the side of the electrode changes the effective surface area of the electrode, hence its output characteristics. When the plastic ceases to hold the carbon electrode firmly against the grease and the metal electrode, the electrical signal transmission characteristics are altered and eventually totally interrupted.

Glassy carbon electrodes are used in other electrochemical analysis and other processes. In some, the carbon itself is used as the electrode. In others, the carbon is used as a carrier for a different electrode material, such as mercury. In these other applications, particularly applications in which the carbon electrode is handled manually, the delicacy of the electrodes, their cost, and short working life are again significant drawbacks.

In accordance with the present invention, a new and improved carbon electrode, parametric sensing system, and disinfectant/sterilizer with improved parametric monitoring are provided.

SUMMARY OF THE INVENTION

In accordance with one aspect to the present invention, a glassy carbon electrode is provided. A compressible insulating sleeve surrounds a glassy carbon rod. The compressible insulating sleeve compresses at a pressure lower than a compressive pressure at which the glassy carbon rod fractures. A ductile sleeve surrounds the insulating sleeve. The ductile sleeve is compressed, compressing the insulating sleeve and providing a fluid tight seal between the ductile sleeve, the insulating sleeve, and the glassy carbon rod.

In accordance with another aspect of the present invention, an electrochemical analyzer cell is provided. An electrochemical analysis chamber defines a fluid receiving reservoir. A plurality of measurement electrodes is disposed in the reservoir to be in electrical contact with solutions received in the reservoir. At least one of the electrodes being a glassy carbon electrode supported and sealed in a metallic sleeve. An analysis control system connected with the electrodes applies at least the currents to the electrodes and reads currents which are indicative of a concentration of a target anolyte.

In accordance with yet another aspect of the present invention, a disinfectant/sterilant system is provided. A chamber receives an item to be disinfected or sterilized. A pump pumps a peroxyacetic acid antimicrobial solution into the chamber. An electrochemical analysis chamber is fluidicly connected to receive the peracetic acid solution flowing to the chamber. The electrochemical analysis chamber defines a fluid receiving reservoir. A plurality of measurement electrodes are disposed in the reservoir to be in electrical contact with solutions received in the reservoir. At least one of the electrodes is a glassy carbon electrode supported and sealed in a metallic sleeve. An analysis control system is connected with the electrodes to apply at least voltages to the electrodes and read currents which are indicative of peroxyacetic acid concentration.

In accordance with yet another aspect of the present invention, an electrochemical method is provided. A glassy carbon rod is surrounded with an insulating sleeve which, in turn, is surrounded by ductile metallic sleeve. The metallic sleeve is compressed forming a fluid tight compression seal with the insulating sleeve and the glassy carbon rod. An electrical connection is made with the glassy carbon rod which compensates for thermal expansion of the metallic sleeves. The electrical connection is connected with an electrochemical analysis system. A face of the glassy carbon rod is immersed into a fluid to be analyzed.

One advantage of the present invention is that it facilitates parametric monitoring of peroxyacetic acid concentration.

Another advantage of the present invention resides in a more durable and longer lived carbon electrode.

Another advantage of the present invention resides in its cost efficiency.

Still further advantages of the present invention will become apparent to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
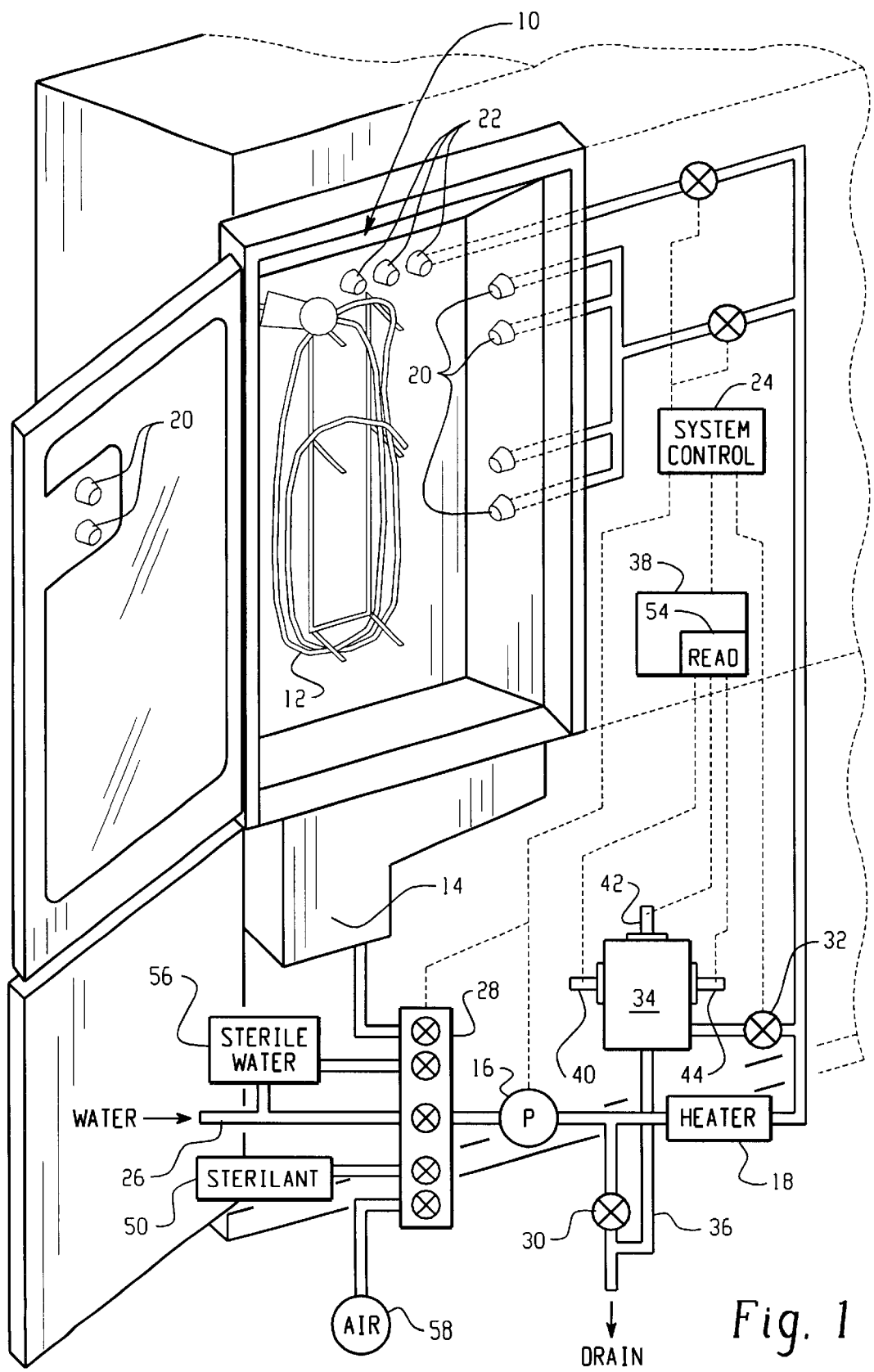
FIG. 1 is a diagrammatic illustration of a liquid disinfection/sterilization system utilizing an electrochemical sensor and carbon electrode in accordance with the present invention.
Figure 2:
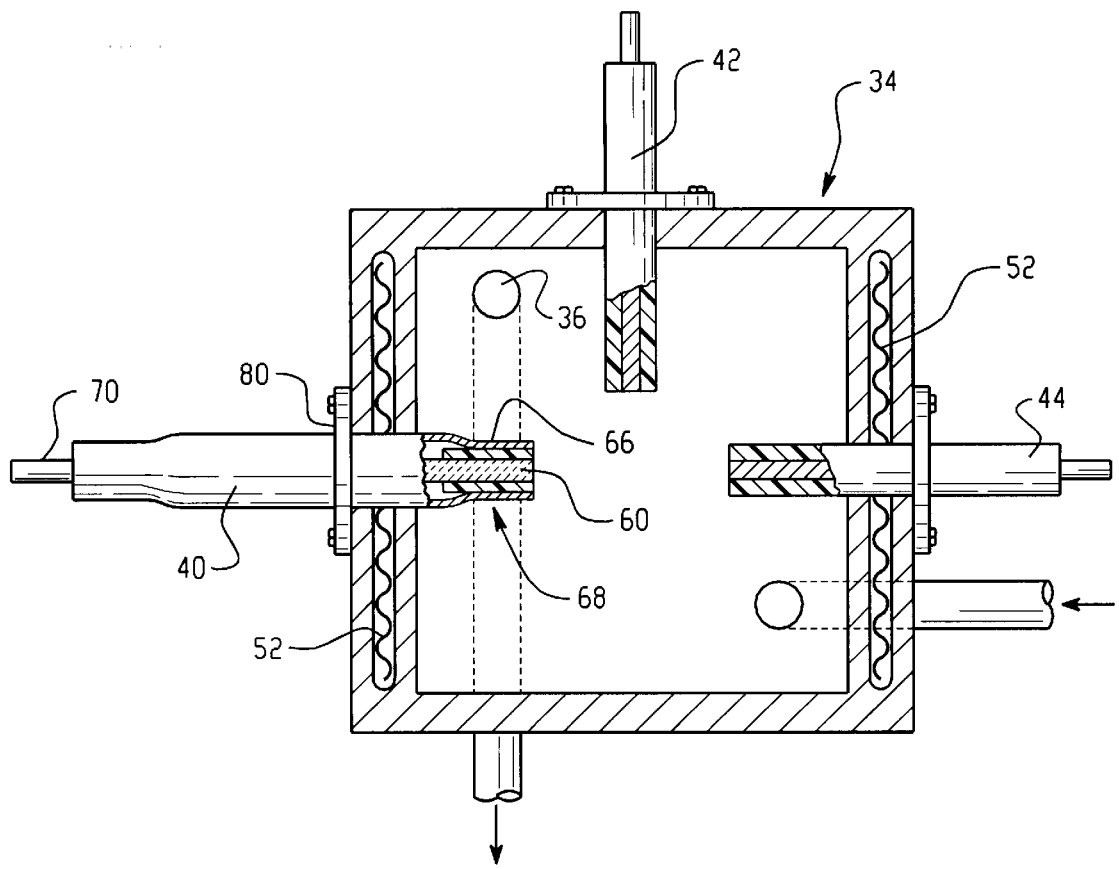
FIG. 2 is an enlarged, cross-sectional view of an electrochemical sensor in accordance with the present invention.

With reference to FIG. 1, a liquid disinfection/sterilization system includes chamber 10 in which an item, such as an endoscope 12 is mounted for sterilization or disinfection. The chamber 10 defines a sump 14 at the bottom where fluid which has been sprayed on the surface of the endoscope or passed through its lumens collects. A pump 16 pumps the liquids from the sump through a heater 18 to nozzles 20 and inlet ports 22 of the chamber. The nozzles 20 spray fluid over the surface of the endoscope and the fluid inlet ports 22 are connected with interior lumens of the endoscope. A system controller 24 controls system components to affect rinsing, cleaning, and sterilization or disinfection operations. Preferably, the system controller controls a water supply 26 to supply water through a manifold valve 28 to the pump to rinse debris from the endoscope. After the initial rinse cycle, a drain valve 30 drains the rinse water from the system. During a wash cycle, the system is again filled with water. Detergent is released from an ampule received in the sump 14 into the water and is again circulated by the pump. At the end of the cleaning cycle, the drain valve again drains the system. Next, the manifold connects the water system to the pump again for another rinse cycle.

After the rinse, water is drained and the system refilled. The ampule releases treatment agents including anticorrosives, buffers, and surfactants into the water. During the circulation of the treatment agents, a sample of the treatment solution is selectively drawn by a valve 32 through an electrochemical analysis chamber 34 to fill an internal reservoir. Preferably, the reservoir is overfilled such that a small amount of fluid goes down a drain line 36 to assure accurate filling. When these agents are received in the analysis chamber, an analysis control system 38 cycles electrical potential to a working electrode 40, a silver/silver chloride or other suitable reference electrode 42, and a non-reactive counter electrode 44. Alternating negative pulses of about −1.5 to −2.5 volts and positive pulses of about +1.5 to +3.5 volts are applied to the working electrode 40 for periods of 1–10 seconds to condition the face of the electrode. Preferably, the negative pulses are about −2.0 volts for about 2 seconds and the positive pulses are about +2.5 volts for about 4 seconds.

After a preselected circulation time, the control circuit 38 causes the release of an antimicrobial agent either in the sump 14 or from a reservoir 50. The antimicrobial agent is added to the solution and circulated over and through the endoscope for a period of time controlled by the analysis controller 38. Once the antimicrobial agent, peroxyacetic acid in the preferred embodiment has been added to the solution, the control system 24 repeatedly causes the valve 32 to open, flushing and refilling the electrochemical analysis chamber reservoir with the antimicrobial solution. Once the electrochemical analysis reservoir has been filled, it is brought to a preselected temperature by a heater 52. Once at temperature, the electrodes are cycled through an about −1.5 to −2.5 volt and about +1.5 to +3.5 volt preparation cycle prior to commencing an electrochemical measurement.

In a preferred measurement procedure, a reference voltage is maintained between the reference and working electrodes by application of a potential to the counter electrode, i.e., a feedback loop maintains the specified voltage between the reference and working electrodes by application of a voltage to the counter electrode, such that current does not flow from the reference electrode. The potential of the counter electrode is typically of greater magnitude than the potential at the reference electrode. Operational amplifiers connected between the reference and counter electrode permit current flow through the sample solution only between the working and counter electrodes. This allows precise control of the applied potential while preventing current from flowing through the reference electrode. The current flowing between the working and counter electrodes is detected by a current monitor or reader 54 in the analysis control system 38 which converts the current into an indication of peracetic acid concentration. In the preferred embodiment, the reader 54 is preprogrammed with a look-up table which correlates current to concentration. At a given temperature, fixed by the heater 52, the measured current is dependent on the concentration of peroxyacetic acid concentration as well as a concentration of other oxidizing species, e.g., hydrogen peroxide. The contributions of these components are dependent on the selected read voltage. In the preferred embodiments, the read voltage is selected in a range of −1.2 to −1.6 volts, more preferably, about −1.4 volts relative to the Ag/AgCl reference electrode. At these potentials, the measurement is relatively insensitive to hydrogen peroxide concentration while being sensitive to peroxyacetic acid concentration. Near the preferred −1.4 voltage, the contribution from hydrogen peroxide concentration is comparable with the contribution from background noise. Hence, the concentration determined by the reader 54 is an accurate measurement of peroxyacetic acid concentration.

After the antimicrobial solution is drained, sterile water from a sterile water source 56 rinses any antimicrobial solution, buffer, or anticorrosive residue from the item 14.

After one or more sterile rinses, a sterile air source 58 blows excess rinse water out of the lumens. Optionally, the sterile air can blow excess liquid off the surface of the endoscope.

Figure 3:
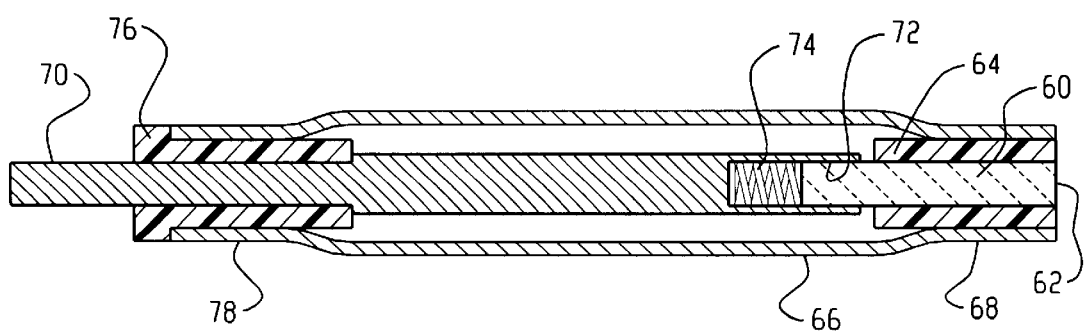
FIG. 3 is a cross-sectional view of a carbon electrode in accordance with the present invention.

Looking now to details of the preferred working electrode and with reference to FIG. 3, the working electrode 40 includes an amorphous glassy carbon rod 60 having an exposed face 62 of preselected area. A glassy carbon is very brittle and relatively easily crushed. The glassy carbon rod is surrounded by a close-fitting polymeric sleeve 64 which is compressible at a compressive force lower than that which fractures the glassy carbon rod and which does not flow significantly, e.g., Teflon™. A metal sleeve 66, which is inert to the material being analyzed, surrounds the polymeric sleeve. For the analysis of strong oxidants, stainless steel is preferred. At one end, the stainless steel sleeve 66 is compressed or swaged 68 into a tight, compressive frictional fit with the Teflon™ polymer, hence the glassy carbon rod. The glassy carbon rod is electrically interconnected with an electrical fitting 70 of preselected geometry, in the preferred embodiment, a rod.

Due to the brittle nature of the glassy carbon rod and the differences in thermal expansion characteristics between stainless steel and typical electrode materials such as brass, a reliable interconnection between a glassy carbon electrode and the conductive rod 70 is not trivial. In the preferred embodiment, the electrically conductive rod 70 has a bore 72 which matches the exterior diameter of the glassy carbon electrode. The glassy carbon electrode is slidably received in the bore providing an electrical interconnection therebetween. Optionally, this interface is lubricated with an electrically conductive grease. A metallic spring 74 is disposed in the bore and compressed between a seat at the bottom of the bore and an end surface of the glassy carbon rod 60. This spring pressure assures electrical interconnection between the glassy carbon rod and the electrically conductive rod.

For complete water tightness and improved durability, another Teflon or other polymeric plug 76 is disposed between the electrical connecting rod 70 and an opposite end of the stainless steel tube 66. This end of the tube is also compressed, e.g., swaged 78, into a compressive watertight seal. Optionally, a mounting flange 80, of appropriate shape and configuration for the analysis chamber or other appliance to which the electrode is to be mounted is welded, brazed, or otherwise connected with the stainless steel tube 66.

After the electrode is assembled, the face 62 of the glassy carbon electrode is polished and a protective overcap is slipped over the swaged end 68 of the stainless steel tube to prevent damage prior to installation.

Although the counter electrode is illustrated as a discrete electrode, it is to be appreciated that the stainless steel tube insulated from the analysis chamber 34 and can be used as the counter electrode 44. The tube 66 can also be made of or plated with other advantageous electrode materials, such as platinum, gold, and the like.

The invention has been described with reference to the preferred embodiment. Obviously, modifications and alterations will occur to others upon reading and understanding the preceding detailed description. It is intended that the invention.be construed as including all such modifications and alterations insofar as they come within the scope of the appended claims or the equivalents thereof.

Having thus described the preferred embodiment, the invention is now claimed to be:

1. A disinfectant/sterilant system comprising:
   a chamber which receives an item to be disinfected or sterilized;
   a pump for pumping a peroxyacetic acid antimicrobial solution into the chamber; and
   an electrochemical analysis chamber fluidly connected to receive the peroxyacetic acid solution flowing to the chamber, the electrochemical analysis chamber including:
   a chamber which defines a fluid receiving reservoir;
   a plurality of measurement electrodes disposed in the reservoir to be in electrical contact with solutions received in the reservoir, at least one of the electrodes including a brittle carbon rod supported and sealed in a metallic sleeve comprising a stainless steel tube, a sleeve of electrically insulating material surrounding the brittle carbon rod, formed of an oxidant-resistant polymer, the insulating sleeve compressing at a force below a compression force which fractures the brittle carbon rod, the metal sleeve being compressed beyond its elastic limit around the insulating sleeve to form a compression fitting with the insulating sleeve and the brittle carbon rod; and
   an analysis control system connected with the electrodes for conducting electrochemical measurements which are indicative of peroxyacetic acid concentration.

2. The system as set forth in claim 1 further including an electrical connector interconnected with the carbon rod.

3. The system as set forth in claim 2 wherein the electrical connector includes a metallic fitting which is supported by and electrically insulated from a second end of the metallic sleeve.

4. The system as set forth in claim 3 wherein a second end of the metallic sleeve is compressed against an insulator sleeve to support and form a fluid-tight seal with the electrical connector.

5. The system as set forth in claim 2 wherein the electrical connector includes:
   an electrically conductive rod that is connected with the carbon rod by an electrically conductive thermal expansion connection assembly.

6. The system as set forth in claim 5 wherein the thermal expansion connection assembly includes:
   a bore defined in the electrically conductive rod which is sized and shaped to receive the carbon rod slidably therein.

7. The system as set forth in claim 1 wherein the metallic sleeve is a second electrode.

8. The system as set forth in claim 1 wherein the carbon is an amorphous carbon.

9. A disinfectant/sterilant system comprising:
   a chamber which receives an item to be disinfected or sterilized;
   a pump for pumping a peroxyacetic acid antimicrobial solution into the chamber; and
   an electrochemical analysis chamber fluidly connected to receive the peroxyacetic acid solution flowing to the chamber, the electrochemical analysis chamber including:
   a chamber which defines a fluid receiving reservoir, and
   a plurality of measurement electrodes disposed in the reservoir to be in electrical contact with solutions received in the reservoir, at least one of the electrodes including a carbon rod supported and sealed in a metallic sleeve, an electrically conductive rod interconnected with the carbon rod by an electrically conductive thermal expansion connection assembly, the thermal expansion connection assembly including:
   a bore defined in the electrically conductive rod which is sized and shaped to receive the carbon rod slidably therein,
   a spring disposed in the bore of the rod in a compressed state to make frictional contact with the electrically conductive rod and the carbon rod; and
   an analysis control system connected with the electrodes for making electrochemical measurements which are indicative of peroxyacetic acid concentration.

10. The system as set forth in claim 9 wherein the insulating sleeve is formed from an oxidant resistant polymer.

11. The system as set forth in claim 9 wherein the carbon is an amorphous glassy carbon.

12. An electrochemical analyzer comprising:
   an electrochemical cell which defines a fluid receiving reservoir;

a plurality of measurement electrodes disposed in the reservoir to be in electrical contact with solutions received in the reservoir, at least one of the electrodes being a carbon electrode including:
  a brittle, carbon rod, an electrically conductive rod supporting an end of the carbon rod,
  a metallic sleeve, the carbon rod being supported and sealed in the metallic sleeve,
  a first sleeve of electrically insulating material surrounding the carbon rod which compresses at a force below a compression force which fractures the carbon rod, the metallic sleeve being compressed around the first insulating sleeve to form a compression fitting with the first insulating sleeve and the carbon rod; and
  a second sleeve of electrically insulating material, the metallic sleeve being compressed around the second insulating sleeve, whereby an electrically insulating, fluid-tight seal is formed with the electrically conductive rod; and
an analysis control system connected with the electrodes for reading at least one of voltages and currents therefrom which are indicative of a concentration of a target composition.

13. The electrochemical analyzer as set forth in claim 12 further comprising a thermal expansion connection assembly interconnecting the electrically conductive rod and the carbon rod, said connection assembly including:
  a bore defined in the electrically conductive rod which is sized and shaped to receive the carbon rod slidably therein.

14. The electrochemical analyzer as set forth in claim 12 wherein the measurement electrodes further include:
  a reference electrode; and
  a counter electrode.

15. The electrochemical analyzer as set forth in claim 14 wherein the metallic sleeve is the counter electrode.

16. The analyzer as set forth in claim 12 wherein the carbon is made of an amorphous carbon.

17. The analyzer as set forth in claim 16 wherein the carbon is a glassy carbon.

18. An electrochemical analyzer comprising:
an electrochemical cell which defines a fluid receiving reservoir;
a plurality of measurement electrodes disposed in the reservoir to be in electrical contact with solutions received in the reservoir, at least one of the electrodes including:
  a carbon rod supported and sealed in a metallic sleeve, an electrically conductive rod interconnected with the carbon rod by an electrically conductive thermal expansion connection assembly, the thermal expansion assembly including:
    a bore defined in the electrically conductive rod which is sized and shaped to receive the carbon rod slidably therein, and
    a spring disposed in the bore of the rod in a compressed state to make electrical contact between the electrically conductive rod and the carbon rod; and
an analysis control system connected with the electrodes.

19. An electrode comprising:
a rod of carbon;
a compressible insulating sleeve surrounding the carbon rod, the compressible insulating sleeve compressing at a pressure lower than a compressive pressure at which the carbon rod fractures;
a ductile sleeve having a first end which surrounds the insulating sleeve, the first end of the ductile sleeve being compressed, compressing the insulating sleeve and providing a fluid-tight seal between the ductile sleeve, the insulating sleeve, and the carbon rod;
an electrical connector interconnected with the carbon rod and supported by a second end of the ductile sleeve, the electrical connector including an electrically conductive element that is directly connected with the carbon rod by an electrically conductive thermal expansion connection assembly.

20. The electrode as set forth in claim 19 wherein the insulating sleeve is made of an inert polymer.

21. The electrode as set forth in claim 20 wherein the ductile sleeve is made of stainless steel.

22. The electrode as set forth in claim 19 wherein the electrically conductive thermal expansion connection assembly includes:
  a bore defined in the electrically conductive element which is sized and shaped to receive the carbon rod slidably therein.

23. The electrode as set forth in claim 22 further including:
  an electrically conductive spring disposed in the bore in a compressed state to make mechanical and electrical contact with the electrically conductive element and the carbon rod.

24. The electrode as set forth in claim 22 wherein a second end of the ductile sleeve is compressed against an insulator sleeve to support and form a fluid-tight seal with the electrically connective element.

25. The electrode as set forth in claim 19 wherein the carbon is an amorphous carbon.

26. The electrode as set forth in claim 25 wherein the carbon is a glassy carbon.

27. An electrode comprising:
a rod of an amorphous form of carbon;
a compressible insulating sleeve surrounding the carbon rod, the compressible insulating sleeve compressing at a pressure lower than a compressive pressure at which the carbon rod fractures;
a ductile sleeve surrounding the insulating sleeve, the ductile sleeve being compressed, compressing the insulating sleeve and providing a fluid-tight seal between the ductile sleeve, the insulating sleeve, and the carbon rod;
an electrical connector supported by the ductile sleeve, a bore defined in the electrically conductive element which is sized and shaped to receive the carbon rod slidably therein; and
a spring, intermediate the electrical connector and the carbon rod, which electrically connects the electrical connector and the carbon rod.

28. An electrochemical method comprising:
surrounding an electrode in the form of a carbon rod with an insulating sleeve;
surrounding the insulating sleeve with a ductile metal sleeve;
compressing the ductile metal sleeve forming a fluid-tight compression seal with the insulating sleeve and the carbon rod;
making an electrical connection with the carbon rod which compensates for thermal expansion of the metallic sleeve;

connecting the electrical connection with an electrochemical analysis system;

immersing at least a face of the carbon rod into a fluid to be analyzed.

29. The method as set forth in claim 28 further including, prior to making an electrochemical measurement, applying alternating conditioning voltage pulses to the carbon electrode.

30. The method as set forth in claim 29 wherein the alternating pulses have magnitudes of +2.5 volts and −2.0 volts.

* * * * *